US007899512B2

(12) United States Patent  
Labadie et al.

(10) Patent No.: US 7,899,512 B2  
(45) Date of Patent: Mar. 1, 2011

(54) SYSTEM AND METHOD FOR SURGICAL INSTRUMENT DISABLEMENT VIA IMAGE-GUIDED POSITION FEEDBACK

(75) Inventors: Robert F. Labadie, Nashville, TN (US); J. Michael Fitzpatrick, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1736 days.

(21) Appl. No.: 11/079,898

(22) Filed: Mar. 14, 2005

(65) Prior Publication Data

US 2005/0228256 A1     Oct. 13, 2005

Related U.S. Application Data

(60) Provisional application No. 60/555,377, filed on Mar. 22, 2004.

(51) Int. Cl.
A61B 5/05          (2006.01)

(52) U.S. Cl. ........................................ 600/407
(58) Field of Classification Search ................ 600/407, 600/411, 414, 426–427, 437, 439, 417; 606/130, 606/1, 10–12, 42; 378/4, 20, 42
See application file for complete search history.

(56) References Cited

U.S. PATENT DOCUMENTS 4,742,815  A  *  5/1988  Ninan et al. ................. 600/118

(Continued)

FOREIGN PATENT DOCUMENTS

DE          10117403 C2     2/2003

OTHER PUBLICATIONS

Bale, R. et al., "Computer-assisted neurosurgery by using a noninvasive vacuum-affixed dental cast that acts as a reference base: another step toward a unified approach in the treatment of brain tumors," *J Neurosurg*, vol. 93, pp. 208-213 (2000).

(Continued)

*Primary Examiner*—Francis Jaworski  
(74) *Attorney, Agent, or Firm*—Morris Manning Martin LLP; Tim Tingkang Xia, Esq.; Christopher W. Glass, Esq.

(57) ABSTRACT

A system for selectively disabling a surgical instrument operating in a surgical site of a region of interest of a living subject. In one embodiment, the system includes means for noninvasively placing a number of fiducial markers in an anatomic space of the region of interest of the living subject, means for pre-operatively measuring a location of each fiducial marker in the anatomic space, an imaging acquisition device for pre-operatively acquiring an image volume from the region of interest of the living subject, a probe for intra-operatively monitoring a location of the surgical instrument in the anatomic space, and a controller configured to perform the steps of identifying a centroid of each fiducial marker in the image volume, registering the identified centroid of each fiducial marker in the image volume to the measured location of the corresponding fiducial marker in the anatomic space to determine a registration transformation, mapping the monitored location of the surgical instrument in the anatomic space onto a corresponding location in the image volume by an inverse of the registration transformation, and generating a signal to disable the surgical instrument when the mapped location of the surgical instrument is substantially close to a boundary of the surgical site of the region of interest in the image volume.

5 Claims, 7 Drawing Sheets

U.S. PATENT DOCUMENTS

| | | | | |
|---|---|---|---|---|
| 4,836,778 | A | * | 6/1989 | Baumrind et al. ............. 433/69 |
| 4,844,063 | A | * | 7/1989 | Clark .......................... 606/39 |
| 5,078,140 | A | * | 1/1992 | Kwoh .......................... 600/417 |
| 5,207,223 | A | * | 5/1993 | Adler .......................... 600/427 |
| 5,474,548 | A | | 12/1995 | Knopp et al. |
| 5,483,961 | A | * | 1/1996 | Kelly et al. .................. 600/429 |
| 5,617,857 | A | * | 4/1997 | Chader et al. ............... 600/424 |
| 5,732,703 | A | * | 3/1998 | Kalfas et al. ................ 600/407 |
| 5,776,064 | A | * | 7/1998 | Kalfas et al. ................ 600/414 |
| 5,799,055 | A | * | 8/1998 | Peshkin et al. ................ 378/42 |
| 5,871,445 | A | * | 2/1999 | Bucholz ..................... 600/407 |
| 5,879,306 | A | * | 3/1999 | Fontenot et al. ............. 600/473 |
| 6,019,724 | A | * | 2/2000 | Gronningsaeter et al. ... 600/439 |
| 6,135,999 | A | * | 10/2000 | Fanton et al. ................. 606/45 |
| 6,201,984 | B1 | * | 3/2001 | Funda et al. ................ 600/407 |
| 6,214,018 | B1 | * | 4/2001 | Kreizman et al. ........... 606/130 |
| 6,236,875 | B1 | * | 5/2001 | Bucholz et al. ............. 600/407 |
| 6,391,028 | B1 | * | 5/2002 | Fanton et al. ................ 606/45 |
| 6,405,072 | B1 | * | 6/2002 | Cosman ...................... 600/426 |
| 6,741,883 | B2 | * | 5/2004 | Gildenberg ................ 600/429 |
| 6,757,582 | B2 | | 6/2004 | Brisson et al. |
| 6,778,850 | B1 | * | 8/2004 | Adler et al. ................. 600/427 |
| 6,810,281 | B2 | * | 10/2004 | Brock et al. ................ 600/427 |
| 6,990,368 | B2 | * | 1/2006 | Simon et al. ................ 600/425 |
| 7,206,626 | B2 | * | 4/2007 | Quaid, III .................... 600/407 |
| 7,206,627 | B2 | * | 4/2007 | Abovitz et al. .............. 600/407 |
| 7,228,165 | B1 | * | 6/2007 | Sullivan ..................... 600/411 |
| 7,313,430 | B2 | * | 12/2007 | Urquhart et al. ............ 600/429 |
| 7,542,791 | B2 | * | 6/2009 | Mire et al. .................. 600/407 |
| 7,567,834 | B2 | * | 7/2009 | Clayton et al. .............. 600/424 |
| 2002/0032453 | A1 | * | 3/2002 | Cosman ...................... 606/130 |
| 2002/0065461 | A1 | * | 5/2002 | Cosman ...................... 600/426 |
| 2002/0120188 | A1 | * | 8/2002 | Brock et al. ................ 600/407 |
| 2004/0034283 | A1 | * | 2/2004 | Quaid, III .................... 600/300 |
| 2004/0034302 | A1 | * | 2/2004 | Abovitz et al. .............. 600/428 |
| 2004/0106916 | A1 | * | 6/2004 | Quaid et al. ................... 606/1 |

OTHER PUBLICATIONS

Casiano, R., "Efficacy of computed radiographic image-guided endoscopic sinus surgery in residency training programs," *Laryngoscope*, vol. 110, pp. 1277-1282 (2000).

Cohen, D. et al., "The prevalence of middle ear pathologies in Jerusalem school children," *Am J Otol*, vol. 10, No. 6, pp. 456-459 (1989).

Farrell, J. et al., "Problem 65-1: A least squares estimate of satellite attitude," *SIAM Rev*, vol. 8, pp. 384-386 (1966).

Fenlon, M. et al., "Locking acrylic resin dental stent for image-guided surgery," *J of Prosthet Dent*, vol. 83, No. 4, pp. 482-485 (2000).

Fried, M. et al. "Image-guided endoscopic surgery: results of accuracy and performance in a multi-center clinical study using an electromagnetic tracking system," *Laryngoscope*, vol. 107, pp. 594-601 (1997).

Galloway, R. et al. "Interactive, Image-Guided Neurosurgery," *IEEE Transactions on BME*, vol. 39, No. 12, pp. 1226-1231 (1992).

Gering, D. et al., "An integrated visualization system for surgical planning and guidance using image fusion and an open MR," *J Magn Reson Imaging*, vol. 13, No. 6, pp. 967-975 (2001).

Herline, A. et al., "Technical advances toward image-guided laparoscopic surgery," *Surg Endosc*, vol. 14, No. 7, pp. 675-679 (2000).

Howard, M., et al., "A noninvasive, reattachable skull fiducial marker system," *J Neurosurg*, vol. 83, pp. 372-376 (1995).

Kemppainen, H., et al., "Epidemiology and aetiology of middle ear cholesteatoma," *Acta Otolaryngol (Stockh)*, vol. 119, pp. 568-572 (1999).

Lunsford, L. et al., "Intra-operative imaging of the brain," *Stereotactic and Functional Neurosurg*, vol. 66, Nos. 1-3, pp. 58-64 (1996).

Maurer, C. et al., "Registration of head volume images using implantable fiducial markers," *IEEE Trans Med Imaging*, vol. 16, No. 4, pp. 447-462 (1997).

Schonemann, P., "A generalized solution of the orthogonal Procrustes problem," *Psychometrika*, vol. 31, pp. 1-10 (1966). Central B F1-P86.

Sibson, R., "Studies in the robustness of multidimensional scaling: perturbational analysis of classical scaling," *J Statis Soc B*, vol. 41, pp. 217-229 (1979).

Spiegel, E. et al., "Stereotactic apparatus for operations on the human brain," *Science*, vol. 106, pp. 349-350 (1947).

Wang, M. et al., "An automatic technique for finding and localizing externally attach ed markers in CT and MR volume images of the head," *IEEE Trans Biomed Eng*, vol. 43, pp. 627-637 (1996).

Weinberg, J. "Surgical management of brain metastases," *Curr Oncol Rep*, vol. 3, No. 6, pp. 476-483 (2001).

West, J. et al. "Comparison and evaluation of retrospective intermodality brain image registration techniques," *J of Computer Assisted Tomography*, vol. 21, No. 4, pp. 554-566 (1997).

West, J. "Fiducial point placement and the accuracy of point-based, rigid-body registration," *Neurosurgery*, vol. 48, pp. 810-817 (2001).

West, J. et al., "The distribution of target error in rigid-body, point-based registration," *IEEE Trans Med Imaging*, vol. 20, pp. 917-927 (2001).

Wisoff, J. et al., "Current neurosurgical management and the impact of the extent of resection in the treatment of malignant gliomas of childhood: a report of the Children's Cancer Group trial No. CCG-945," *J of Neurosurg*, vol. 89, No. 1, pp. 52-59 (1998).

Strauss, Gero et al., "The Navigation-Controlled Drill in Temporal Bone Surgery: A Feasibility Study," *The Laryngoscope*, vol. 117; Mar. 2007, pp. 434-441.

* cited by examiner

SYSTEM AND METHOD FOR SURGICAL INSTRUMENT DISABLEMENT VIA IMAGE-GUIDED POSITION FEEDBACK

CROSS-REFERENCE TO RELATED PATENT APPLICATION

This application claims the benefit, pursuant to 35 U.S.C. §119(e), of provisional U.S. patent application Ser. No. 60/555,377, filed Mar. 22, 2004, entitled "SURGICAL INSTRUMENT DISABLEMENT VIA IMAGE-GUIDED POSITION FEEDBACK," by Robert F. Labadie, and J. Michael Fitzpatrick, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [7] represents the 7th reference cited in the reference list, namely, West J B, Fitzpatrick J M, Toms S, Maurer, Jr, and Maciunas R J. Fiducial point placement and the accuracy of point-based, rigid-body registration. *Neurosurgery* 48: 810-817, 2001.

STATEMENT OF FEDERALLY-SPONSORED RESEARCH

The present invention was made with Government support under Grant No. R21 EB02886-02 awarded by the National Institutes of Health. The United States Government may have has certain rights to this invention pursuant to this grant.

FIELD OF THE INVENTION

The present invention generally relates to a computer-assisted surgery and in particular to the utilization of a feedback trigger during a surgery to selectively disable a surgical instrument operating in a region of interest of a living subject.

BACKGROUND OF THE INVENTION

Radiographic imaging is often imperative for the pre-operative planning of surgical treatments for patients. Plain X-rays, computed tomography (hereinafter "CT") images, and magnetic resonance (hereinafter "MR") images facilitate surgical navigations. Because of their usefulness, surgeons have sought innovative ways to further incorporate radiographic imaging into the surgical suite. For years, orthopedic and vascular surgeons have relied upon intra-operative, real-time fluoroscopy, such as plain X-rays, to assess surgical treatments. More recently, real-time MR [1] and CT [2] imaging surgical suites have been constructed where intra-operative MR or CT image is continuously updated displaying anatomic changes due to surgical treatment. These systems have found limited use due to logistic difficulties including the exorbitant cost of a dedicated CT or MR imaging system in an operative suite and the physically confined environment in which a surgeon operates.

A more feasible option has been the use of pre-operative CT and/or MR images in an image-guided surgery (hereinafter "IGS") where anatomic locations are continuously updated on the pre-operative CT and/or MR images as specified by a surgical probe. The concept of the image-guided surgery dated back to the 1940's [3]. However, widespread acceptance of the concept did not occur until radiographic advances in the 1970's that made CT and MR images routinely available. Image-guided surgical systems, which are analogous to global-positioning systems (hereinafter "GPS"), have since found widespread use in neurosurgery [4] and sinus surgery [5]. In general, An IGS system includes a pre-operative radiographic image (CT or MR image) that is acquired from a patient and digitized and stored on a computer. Within the operating room (hereinafter "OR"), the pre-operative radiographic image are registered to the anesthetized patient by correlating landmarks found on the pre-operative radiographic image with the landmarks on the anesthetized patient. Typical landmarks used for registration are anatomic points and/or fiducial markers attached to the skin or implanted in bone of a patient. Registration creates a transformation matrix that allows a direct mapping of the patient's current anatomy to the corresponding pre-operative radiographic image. Once registration has taken place, for example, using an electronically visible probe, such as infrared optical system and/or electromagnetic system, to detect a location of each fiducial marker in the patient, i.e., the physical space, that is registered to in a radiographic image space. The probe can be used as a pointer to identify surgical anatomy on CT or MR images.

Crucial to limiting error in IGS systems is registration of the pre-operative radiographic image to the surgical field of interest in the anesthetized patient. Registration landmarks, for example, anatomic landmarks and/or fiducial markers, need to be immobile relative to the anatomy and arranged such that they surround the surgical field of interest. While multiple anatomic landmarks would initially appear useful, soft tissue, for instance, skin and muscle, relaxes and distorts under general anesthesia making boney landmarks necessary for accurate registration. A solution has been to implant markers into bone of a patient. This is routinely used in neurosurgery where screws are placed into the cranium prior to pre-operative radiographic imaging and these screws serve as landmarks for registration. While accuracy with such systems is impressive [6, 7], it does involve the invasive placement of bone screws with small, yet real, risk of infection and cosmetic deformity. Another solution is to use skin markers or skin contours. Such systems have shown decreased accuracy that is unacceptable in otologic applications [8].

The most common ear disorders of human being that require surgical treatments are chronic serous otitis media (hereinafter "CSOM") and cholesteatoma. The CSOM is characterized by inflammation of the mucous membrane lining the middle ear that does not respond to medical therapy. The cholesteatoma contains keratinizing squamous epithelium (skin) trapped within the middle ear cavity and leads to chronic infection, hearing loss, facial nerve paralysis, and vertigo. Both the CSOM and cholesteatoma are usually treated by an otologic surgery, for example, through a mastoidectomy, to remove diseased tissues from the temporal bone encasing the ear using a surgical drill and/or knife. As a result, adjacent structures surrounding the surgical site of the temporal bone, such as the facial nerve, the inner ear, the floor of the cranial vault, the internal jugular vein and the carotid artery, are at great risk during the surgical treatment.

It has been shown that IGS systems can improve overall standards of surgical treatments in both neurosurgery and sinus surgery. Specifically, IGS systems have improved surgical accuracy and reduce the risk of major complications in sinus surgery [9], and decreased operative time for neurosurgical procedures thus cutting costs [10]. In addition, patients treated with an IGS have more complete resection of diseased tissues with less collateral damage to healthy tissues [11] than that treated with a traditional surgery. It is anticipated that such advantages of the IGS systems would be also applicable to an otologic surgery. Epidemiologic and economic data supports the usefulness of an IGS in otologic procedures. However, applications have been limited by the need for millimeter and sub-millimeter accuracies to prevent injury to adjacent structures, such as the facial nerve and the inner ear.

Therefore, a heretofore unaddressed need still exists in the art to address the aforementioned deficiencies and inadequacies.

SUMMARY OF THE INVENTION

The present invention, in one aspect, relates to a system for selectively disabling a surgical instrument operating in a surgical site of a region of interest of a living subject, where the surgical instrument has a distal end portion. The present invention can be practiced with respect to several surgical instruments and any combinations of them. As non-limiting examples, the surgical instrument can be a drill, and the distal end portion of the surgical instrument is the tip of the drill. The surgical instrument can be a surgical scalpel, and the distal end portion of the surgical instrument is the cutting portion of the surgical scalpel. The surgical instrument can also be a suction device, and the distal end portion of the surgical instrument is the sucking portion of the suction device. The region of interest of the living subject may correspond to an ear portion, a mouth portion, a head portion, or other body portions of the living subject.

In one embodiment, the system includes means for noninvasively placing a number, M, of fiducial markers in an anatomic space of the region of interest of the living subject. The placing means has a locking dental acrylic resin splint (hereinafter "LADS") mountable to a maxilla of the living subject, where the LADS includes a central portion with an extension at a predetermined position, and two lateral portions attached to the central portion. The placing means further has a fiducial frame attachable to the LADS by the extension for receiving the number M of fiducial markers. The fiducial frame comprises a frame structure, a first panel and an opposite, second panel extending upwardly from the frame structure, each of the first panel and the second panel defining a number of holes for receiving a corresponding number of fiducial markers. The fiducial frame is configured such that when the number M of fiducial markers are received therein, the centroid of each fiducial marker approximates the surgical site of the ear portion of the living subject and distance between at least one pair of two corresponding fiducial markers is maximized so as to minimize a target registration error.

The system further includes means for pre-operatively measuring a location of each fiducial marker in the anatomic space of the region of interest of the living subject, an imaging acquisition device for pre-operatively acquiring an image volume from the region of interest of the living subject, where the pre-operatively acquired image volume includes the image of at least two of M fiducial markers, and a probe operatively coupled with the surgical instrument for intra-operatively monitoring a location of the distal end portion of the surgical instrument in the anatomic space of the region of interest of the living subject. Moreover, the system includes a controller operatively coupled with the measuring means, the imaging acquisition device, the probe, and the surgical instrument, respectively. The controller is configured to perform the steps of identifying a centroid of each fiducial marker in the pre-operatively acquired image volume, registering the identified centroid of each fiducial marker in the pre-operatively acquired image volume to the pre-operatively measured location of the corresponding fiducial marker in the anatomic space so as to determine a registration transformation, mapping the intra-operatively monitored location of the distal end portion of the surgical instrument in the anatomic space onto a corresponding location in the pre-operatively acquired image volume by an inverse of the registration transformation, and generating a signal to disable the surgical instrument when the mapped location of the distal end portion of the surgical instrument is substantially close to a boundary of the surgical site of the region of interest in the pre-operatively acquired image volume. Furthermore, the system includes a number, N, of surgical markers, each placed in a surgically significant anatomic location serving as a registration target.

Moreover, the system has an alarm device communicating with the controller for generating an alarm when the mapped location of the distal end portion of the surgical instrument is within a predetermined distance to the boundary of the surgical site in the region of interest in the pre-operatively acquired image volume. Additionally, the system includes an interlock device operatively associated with the surgical instrument and communicating with the controller, where the interlock device disables the surgical instrument when the mapped location of the distal end portion of the surgical instrument is within a predetermined distance to the boundary of the surgical site in the region of interest in the pre-operatively acquired image volume.

In another aspect, the present invention relates to a method for selectively disabling a surgical instrument operating in a surgical site of a region of interest of a living subject, where the surgical instrument has a distal end portion, the region of interest of the living subject is surrounded with a plurality of markers. The plurality of markers includes a number, M, of fiducial markers determining an image registration and a number, N, of surgical markers with each surgical marker placed in a surgically significant anatomic location serving as a registration target. The region of interest of the living subject corresponds to an ear portion of the living subject.

In one embodiment, the method includes the step of pre-operatively acquiring an image volume from the region of interest of the living subject, where the pre-operatively acquired image volume contains the image of at least two of M fiducial markers. Furthermore, the method has the steps of identifying a centroid of each fiducial marker from the pre-operatively acquired image volume, pre-operatively measuring a location of each fiducial marker in an anatomic space of the region of interest of the living subject, registering the identified centroid of each fiducial marker in the pre-operatively acquired image volume to the pre-operatively measured location of the corresponding fiducial marker in the anatomic space so as to determine a registration transformation, intra-operatively monitoring a location of the distal end portion of the surgical instrument in the anatomic space of the region of interest of the living subject, and mapping the intra-operatively monitored location of the distal end portion of the surgical instrument in the anatomic space onto a corresponding location in the pre-operatively acquired image volume by an inverse of the registration transformation. Moreover, the method includes the step of generating a signal to disable the surgical instrument when the mapped location of the distal end portion of the surgical instrument is substantially close to a boundary of the surgical site of the region of interest of the living subject in the pre-operatively acquired image volume.

In one embodiment, the method further has the step of mounting an LADS with an attached fiducial frame onto a maxilla of the living subject, where the fiducial frame is configured such that when the number M of fiducial markers are received therein, the centroid of each fiducial marker approximates the surgical site of the ear portion of the living subject and distance between at least one pair of two corresponding fiducial markers is maximized so as to minimize a target registration error. Additionally, the method has the step of generating an alarm when the mapped location of the surgical instrument is within a predetermined distance to the boundary of the surgical site in the pre-operatively acquired image volume.

In yet another aspect, the present invention relates to a system for selectively disabling a surgical instrument operating in a surgical site of a region of interest of a living subject, where the surgical instrument has a distal end portion and is operable by a surgeon during a surgery. In one embodiment, the system has an eye-tracking device operatively coupled with the surgical instrument for intra-operatively tracking the visual line of sight of the surgeon and a location of the distal end portion of the surgical instrument in the region of interest of the living subject, respectively, and a controller operatively coupled with the surgical instrument and the eye-tracking device, respectively. The controller is configured to perform during the surgery the steps of determining an angle between a visual path connecting a predetermined point of the eye-tracking device and the distal end portion of the surgical instrument in the region of interest of the living subject and the line of sight of the surgeon, and generating a signal to disable the surgical instrument when the angle is larger than a predetermined angle. In one embodiment, the eye-tracking device includes a head-hold device and has a sensor.

The system, in one embodiment, has a display communicating with the controller and the eye-tracking device for displaying the tracked line of sight of the surgeon and the tracked location of the distal end portion of the surgical instrument in the region of interest of the living subject, respectively.

In a further aspect, the present invention relates to a method for selectively disabling a surgical instrument operating in a surgical site of a region of interest of a living subject, where the surgical instrument has a distal end portion and is operable by a surgeon during a surgery. In one embodiment, the method includes the steps of intra-operatively tracking the visual line of sight of the surgeon and a location of the distal end portion of the surgical instrument in the region of interest of the living subject, respectively, determining an angle between a visual path connecting a predetermined point of the eye-tracking device and the distal end portion of the surgical instrument in the region of interest of the living subject and the line of sight of the surgeon, and generating a signal to disable the surgical instrument when the angle is larger than a predetermined angle.

In yet a further aspect, the present invention relates to a system for selectively disabling a surgical instrument operating in a surgical site of a region of interest of a living subject, where the surgical instrument has a distal end portion and is operable by a surgeon during a surgery. In one embodiment, the system has a probe for intra-operatively monitoring an electrophysiological condition of the living subject in the region of interest, and a controller operatively coupled with the surgical instrument and the probe, respectively. The controller is configured to perform during the surgery the steps of determining a variation of the electrophysiological condition of the living subject from an initial state of the living subject in the region of interest, and generating a signal to disable the surgical instrument when the variation of the electrophysiological condition is greater then a predetermined value.

The system further has at least one of a display and an audio device for visually and/or audibly displaying the intra-operatively monitored electrophysiological condition of the living subject in the region of interest, respectively.

In one embodiment, the probe comprises at least one needle electrode placed in the region of interest of the living subject, and the electrophysiological condition comprises an electromyogram of electrical activities of muscles of the region of interest of the living subject. In another embodiment, the probe comprises a Doppler vascular probe, and the electrophysiological condition includes a flow rate of blood vessels of the region of interest of the living subject. In an alternative embodiment, the probe has a temperature-sensing device, and the electrophysiological condition includes a temperature of tissues of the region of interest of the living subject. In one embodiment, the probe has an oxygenation detector, and the electrophysiological condition comprises a venous oxygenation saturation and an arterial oxygenation saturation of the region of interest of the living subject. In another embodiment, the probe includes a tissue boundary detector, where the tissue boundary detector comprises at least one of an ultrasound sensing device, an infrared radiation sensing device, an ultraviolet radiation sensing device, a fluorescent radiation sensing device, and a video frame device. The electrophysiological condition includes a tissue type identification of tissues at the distal end portion of the surgical instrument in the region of interest of the living subject. The electrophysiological condition may also relate to a volume of suction from the region of interest of the living subject.

In one aspect, the present invention relates to a method for selectively disabling a surgical instrument operating in a surgical site of a region of interest of a living subject, where the surgical instrument has a distal end portion and is operable by a surgeon during a surgery. In one embodiment, the method includes the steps of intra-operatively monitoring the electrophysiological condition of the living subject in the region of interest, determining a variation of the electrophysiological condition of the living subject from an initial state of the living subject in the region of interest, and generating a signal to disable the surgical instrument when the variation of the electrophysiological condition is greater than a predetermined value.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Figure 1B:
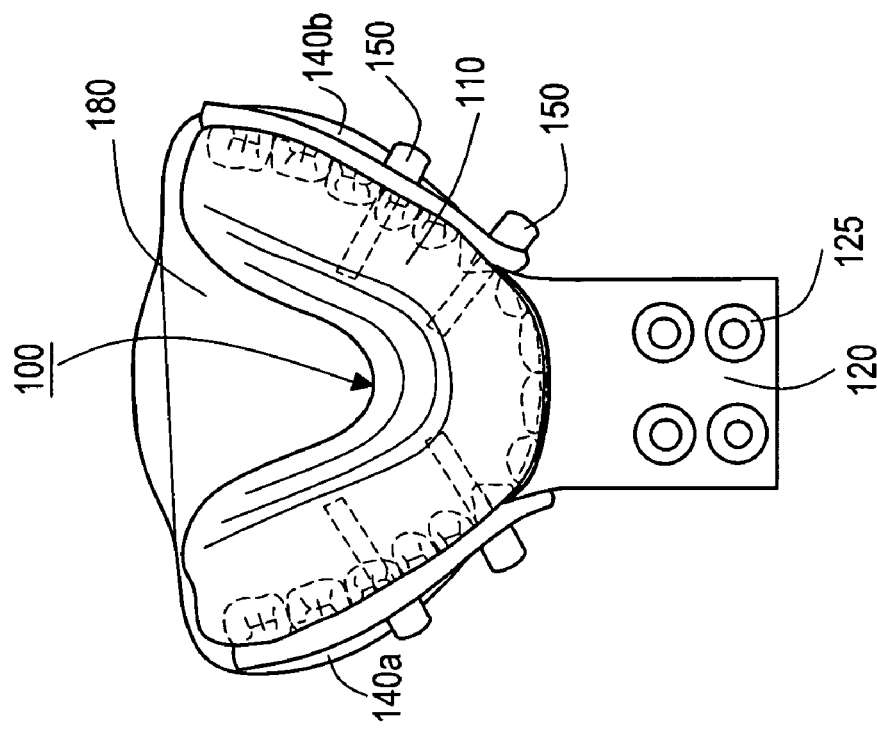
FIG. 1 shows a perspective view of a LADS according to one embodiment of the present invention: (A) the LADS dismissed, and (B) the LADS mounted to a maxilla of a human anatomy.

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The description will be made as to the embodiments of the present invention in conjunction with the accompanying drawings 1-6. In accordance with the purposes of this invention, as embodied and broadly described herein, this invention, in one aspect, relates to a system for selectively disabling a surgical instrument operating in a surgical site of a region of interest of a living subject. The living subject can be a human patient or an animal. In one embodiment, a human patient is employed to practice the current invention, a region of interest of the patient corresponds to an ear portion of the patient, and the surgical instrument having a distal end portion and is operable by a surgeon during a surgery.

Figure 6:
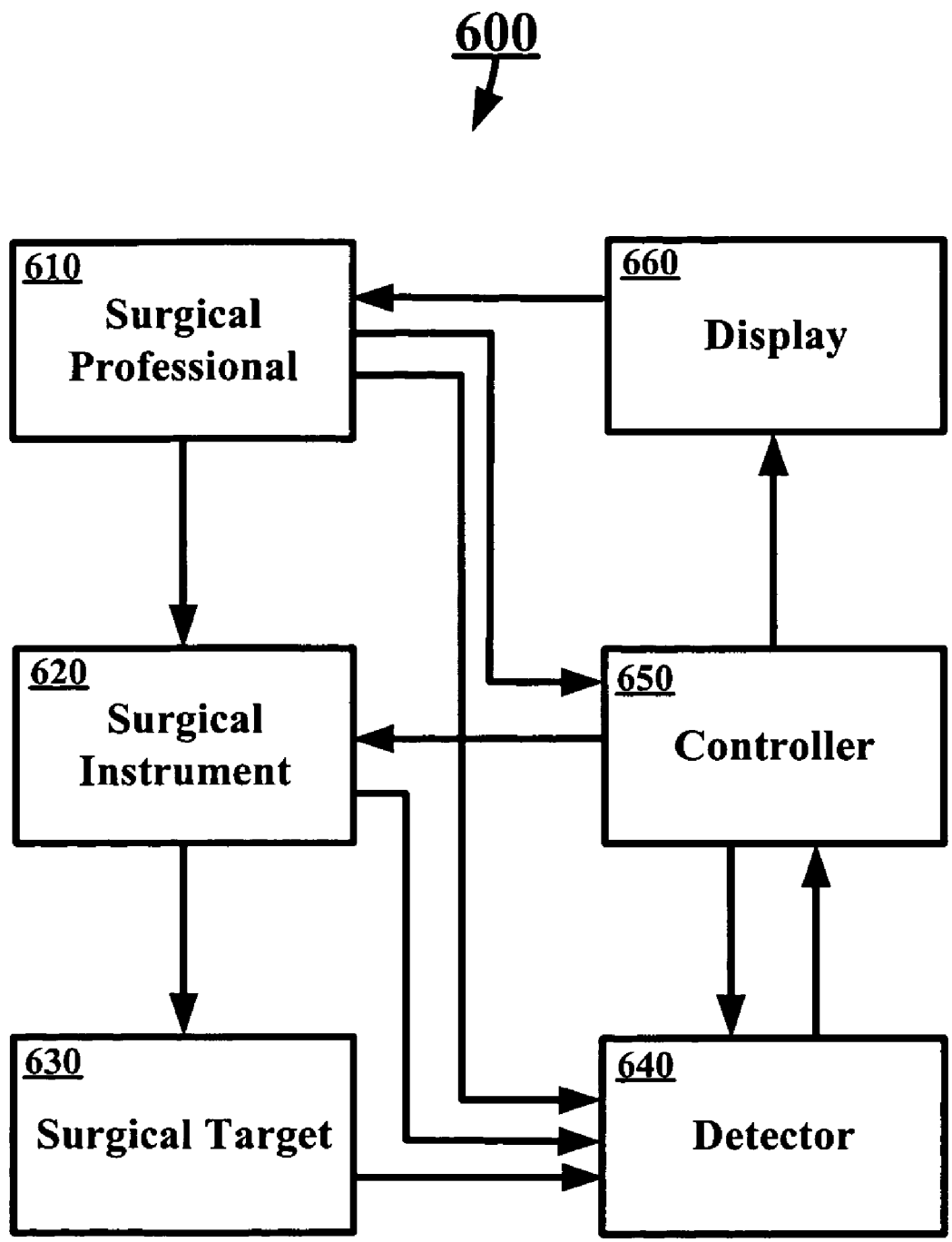
FIG. 6 shows schematically a block diagram for a system for selectively disabling a surgical instrument operating in a surgical target of a living subject according to one embodiment of the present invention.

Referring first to FIG. 6, a block diagram for a system 600 is schematically shown. In general, the system 600 can be utilized by at least one surgical professional 610 for operating a surgery on a surgical target, which may includes pre-operatively surgery planning, intra-operatively surgery operation and post-operatively surgery evaluation. The system 600 includes a surgical instrument 620 operable by the at least one surgical professional 610 for operating the surgery with respect to the surgical target 630. The system 600 further has a detector 640 communicatable with the at least one surgical professional 610, the surgical instrument 620 and the surgical target 630, for intra-operatively detecting a visual condition of the surgical professional 610, a location of the surgical instrument 620, and an electrophysiological condition of the surgical target 630, respectively. Moreover, the system 600 has a controller 650 communicating with the detector 640, and the surgical instrument 620, respectively, for receiving data from the detector 640, processing them therein and generating a signal to disable the surgical instrument 620 when a predetermined condition in the processed data is identified, as further described below. The controller 650 is programmable by the surgical professional 610 or other authorized users such as surgical assistants. Furthermore, the system 600 includes a display 660 communicatable with the controller 650 for intra-operatively displaying the detected visual condition of sight of the at least one surgical professional 610, the location of the surgical instrument 620, and the electrophysiological condition of the living subject in the surgical target 630, respectively. The information on the display 660 is available to the at least one surgical professional 610 or surgical assistants.

Figure 1A:
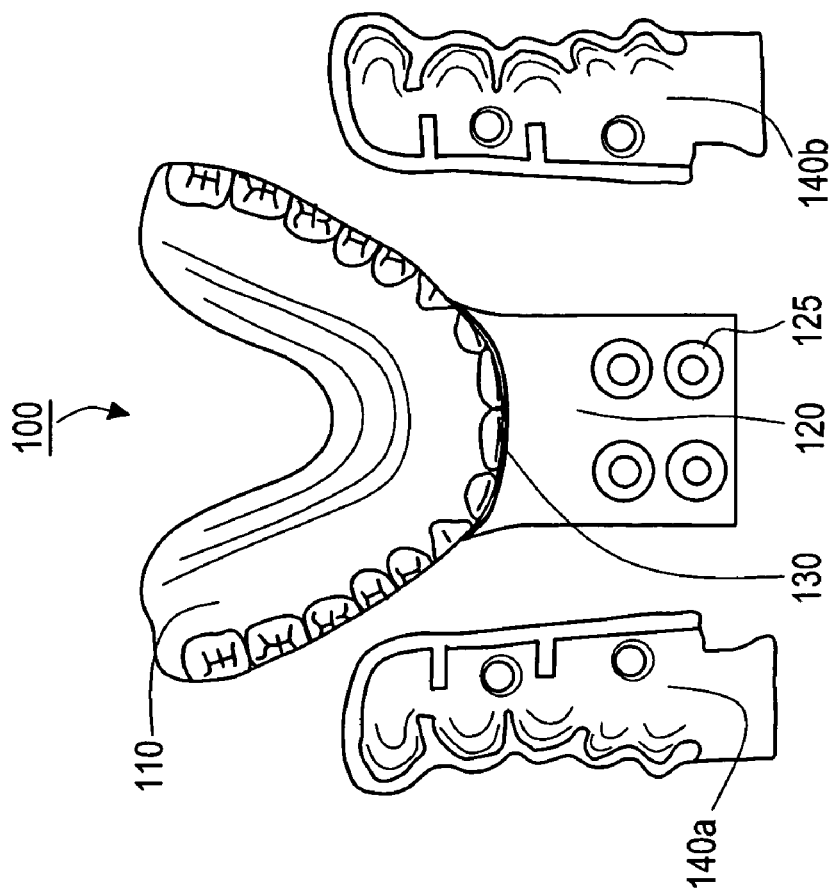

Specifically, the system, in one embodiment, includes means for noninvasively placing a number, M, of fiducial markers in an anatomic space of the ear portion of a patient. Referring in general to FIGS. 1-3, and in particular to FIG. 1, the placing means includes a LADS 100 (Peterman Dental Lab, Nashville, Tenn.) that is mounted onto a maxilla 180 of the patient. The LADS 100 is in the form of a dental biteblock that may be customizedly molded for individual maxillary dental patterns. The LADS 100 has a central portion 110 that imprints the lingual and occlusal surfaces of the maxillary teeth with an extension 120 at a predetermined position 130 and two lateral portions 140a and 140b that imprint the buccal surfaces and are attached to the central portion 110, respectively. The extension 120 has mounting means 125, which in this embodiment has one or more mounting holes formed on the extension 120. The central portion 110 and lateral portions 140a and 140b are secured onto the maxilla 180 using one or more screws 150 that hold the lateral portions 140a and 140b securely with the central portion 110 in cooperation with corresponding mounting holes 125. The geometry of the teeth, being narrower at the insertion into the gums, ensures a tight, reliable fit.

Figure 2A:
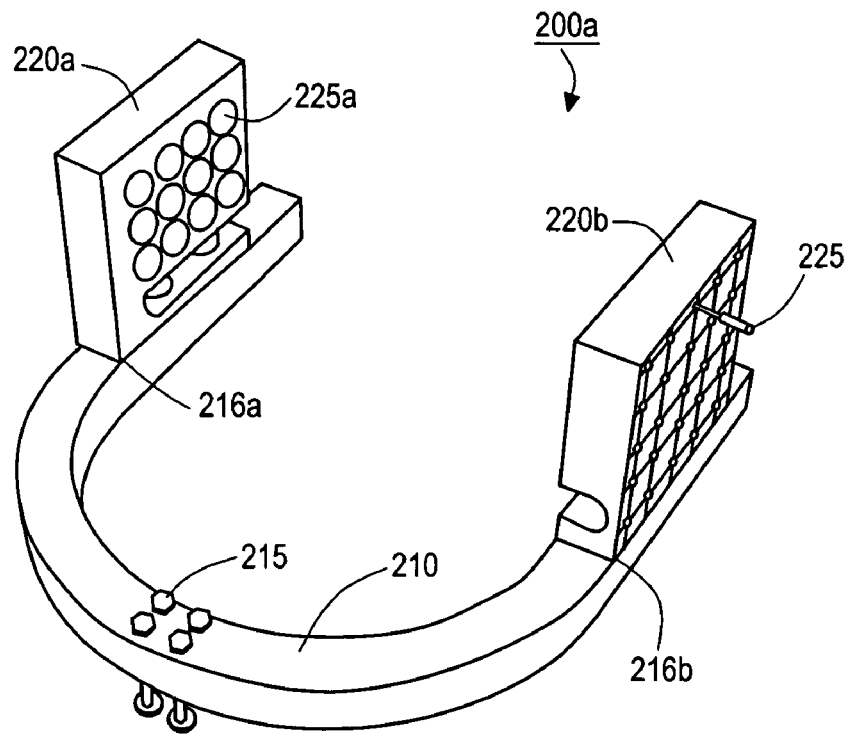
FIG. 2 shows a perspective view of a fiducial frame: (A) the fiducial frame according to one embodiment of the present invention, (B) the fiducial frame according to another embodiment, and (C) the fiducial frame according to an alternative embodiment.

The placing means further includes a fiducial frame that is attached to the LADS by the extension for receiving the number M of fiducial markers. Referring now to FIG. 2A, in one embodiment, a fiducial frame 200a includes a U-shaped frame structure 210 having a first end portion 216a and a second end portion 216b, a first panel 220a extending upwardly from the first end portion 216a of the frame structure 210, and an opposite, second panel 220b extending upwardly from the second end portion 216b of the frame structure 210. Each of the first panel 220a and the second panel 220b has one or more holes formed therein for receiving corresponding marker(s) 225. In one embodiment, commercially available markers 225 (Acustar®, Z-Kat, Inc., Hollywood, Fla.) are received into the holes and mounted on the first panel 220a and the second panel 220b of the fiducial frame 200a, respectively. The fiducial frame 200a further has an engagement projection 215 located at a predetermined position in the frame structure 210 for engaging the fiducial frame 200a to the LADS 100 through corresponding mounting means 125.

Figure 2B:
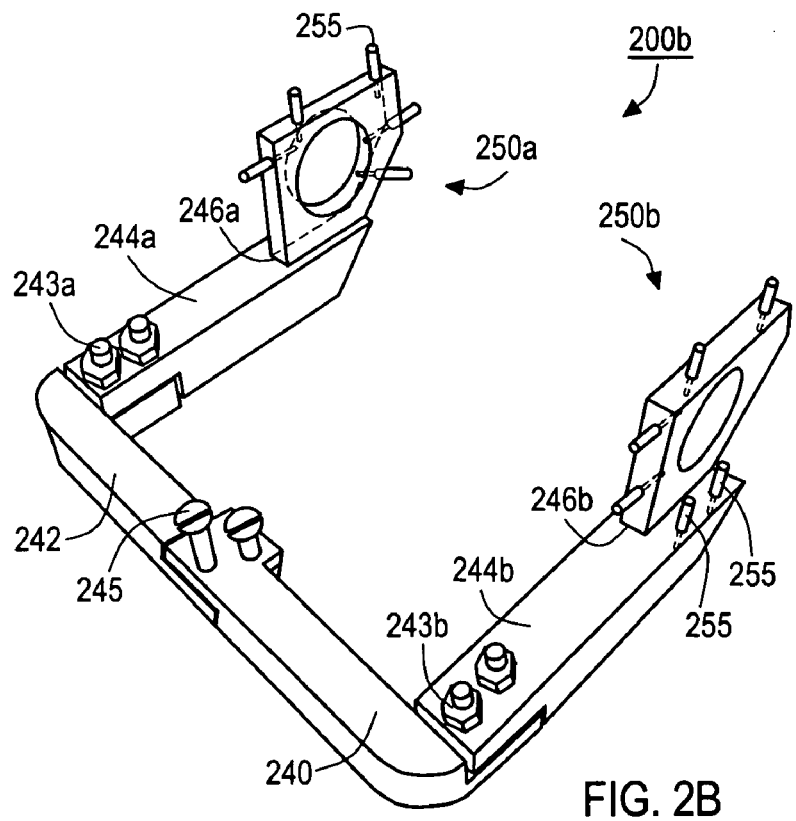

Referring to FIG. 2B, a fiducial frame 200b is shown according to another embodiment of the present invention. The fiducial frame 200b has a frame structure 240. The frame structure 240 includes a first arm 244a, a second arm 244b, a shoulder 242 connecting the first arm 244a and the second arm 244b, a first adjusting means 243a located in the junction of the shoulder 242 and the first arm 244a, and a second adjusting means 243b located in the junction of the shoulder 242 and the second arm 243b. The first arm 244a has an end portion 246a, and the second arm 244b has an end portion 246b. The fiducial frame 200b further has a first panel 250a and an opposite, second panels 250b respectively extending upwardly from the end portions 246a and 246b of the first arm 244a and the second arm 244b of the frame structure 240. Each of the first panel 250a and the second panel 250b is structured to receive several corresponding fiducial markers 255. The fiducial frame 200b further has an engagement projection 245 located at a predetermined position in the shoulder 242 of the frame structure 210 for engaging the fiducial frame 200b to the LADS 100 through corresponding mounting means 125. In this embodiment, the size of the fiducial frame 200b can be adjusted by the adjusting means 243a and 243b to accommodate skulls of varying dimensions of a living subject.

Figure 2C:
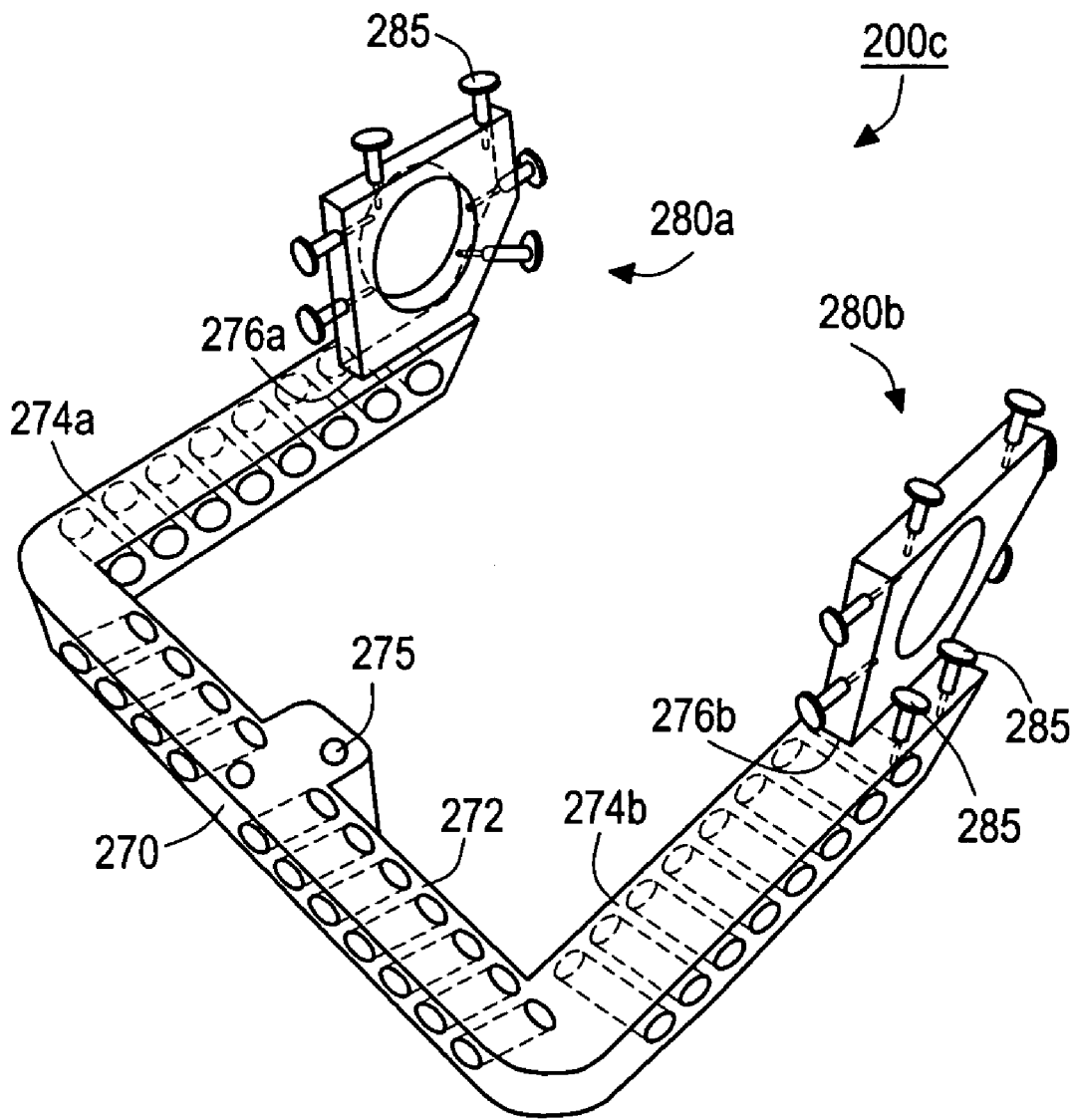

FIG. 2C shows a fiducial frame 200c according to an alternative embodiment of the present invention. The fiducial frame 200c includes a frame structure 270 that has a shoulder 272, a first arm 274a and a second arm 274b extending from the shoulder 272, respectively. The first arm 274a has an end portion 276a, and the second arm 274b has an end portion 276b. The fiducial frame 200c further has a first panel 280a and an opposite, second panels 280b respectively extending upwardly from the end portions 276a and 276b of the first arm 274a and the second arm 274b of the frame structure 270. Each of the first panel 280a and the second panel 280b is structured to receive several corresponding fiducial markers 285. The fiducial frame 200c further has an engagement projection 275 located at a predetermined position in the shoulder 272 of the frame structure 270 for engaging the fiducial frame 200c to the LADS 100 through corresponding mounting means 125. The fiducial frame 200c is featured at minimizing weight and optimizing the number of fiducial markers necessary to achieve sub-millimeter accuracy.

A fiducial frame is made of materials such that the fiducial frame is considered as a rigid-body, i.e., no appreciable deformity under normal use, and has a weight minimized so as to prevent excess torques that may injure dentition. In one embodiment, spun carbon fibers are used to construct the fiducial frame, which minimize weight while maximizing rigidity of the fiducial frame.

Figure 3A:
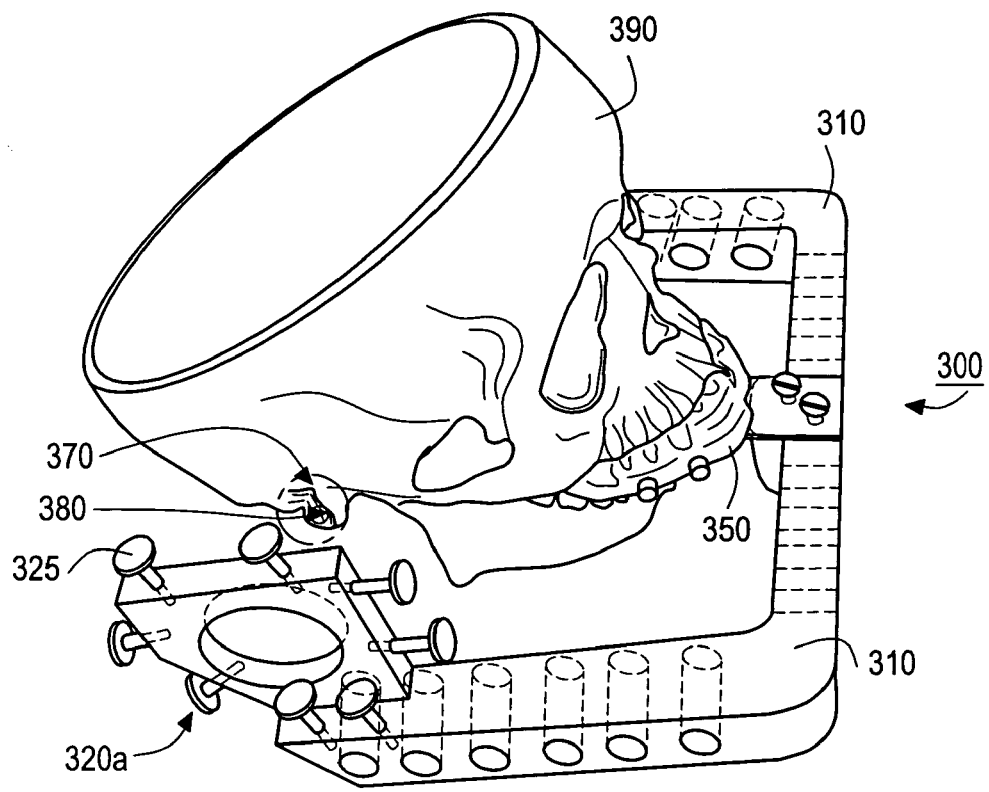
FIG. 3 shows a perspective view of placing means including a LADS and a fiducial frame mounted to a skull of a human anatomy according to one embodiment of the present invention: (A) a side perspective view, and (B) a front perspective view.
Figure 3B:
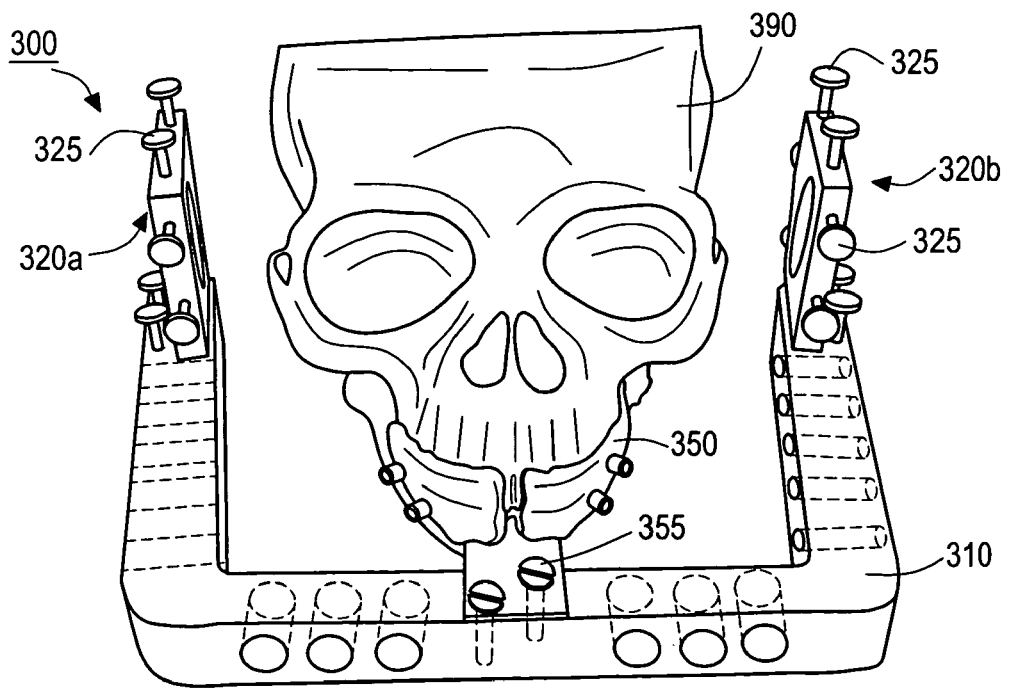

Referring to FIGS. 3A and 3B, a placing means 300 is secured to a skull 390 of a human by mounting a LADS 350 onto the maxilla. In this embodiment, a fiducial frame 310 shown in FIG. 2C is attached to the LADS 350 by mounting means 355. The fiducial frame 310 is configured such that when a number of fiducial markers 325 are received in the first panel 320a and the second panel 320b, respectively, the centroid of each fiducial marker 325 approximates a predetermined surgical site 380 in the ear portion 370 of the human and the distance between the corresponding fiducial markers 325 positioned in each of the first panel 320a and the second panel 320b is maximized so as to minimize a TRE. Rigid fixation of fiducial markers to the first panel 320a and the second panel 320b is advantageous because it avoids drilling into the skull. In one embodiment, nine fiducial markers, such as Acustar® of Z-Kat, Inc., are received in each of the first panel 320a and the second panel 320b of the fiducial frame 310. The eighteen markers are served as fiducial markers for registration.

Furthermore, the system includes an image acquisition device (not shown), such as a CT imaging scanner or a MR imaging scanner, for pre-operatively acquiring an image volume, i.e., a three-dimensional (hereinafter "3D") radiographic image, which contains the eighteen fiducial markers from the ear portion of the patient. In one embodiment, the image volume, such a CT image, is acquired using clinically applicable, temporal-bone algorithms with scan thickness of about 0.5 mm. Moreover, the system includes means for pre-operatively measuring a location of each fiducial marker in the anatomic space of the ear potion of the patient. In one embodiment, a commercially available infrared optical tracking system (Polaris®, Northern Digital Corp., Waterloo, Canada) is employed to measure the location of each fiducial marker in the anatomic space of the ear potion of the patient. Other tracking systems can also be used to practice the current invention. The system further includes a surgical probe operatively coupled with the surgical instrument to detect a location of the distal end portion of the surgical instrument in anatomic space of the ear portion of the patient during the surgical treatment. In one embodiment, the surgical probe comprises an infrared optical tracking system, and the surgical instrument includes a high-speed surgical drill fitted with infrared emitters that is visible to the infrared optical tracking system.

Additionally, the system includes a controller operatively coupled with the image acquisition device, the measuring means and the surgical probe, respectively. The controller in one embodiment includes a computer and is configured to (i) identify a centroid of each fiducial marker in the pre-operatively acquired 3D radiographic image, for example, a CT image volume, (ii) register the identified centroid of each fiducial marker in the pre-operatively acquired 3D radiographic image to the pre-operatively measured location of the corresponding fiducial marker in the anatomic space so as to determine a registration transformation, (iii) map the intra-operatively monitored location of the distal end portion of the surgical instrument in the anatomic space onto a corresponding location in the pre-operatively acquired 3D radiographic image by an inverse of the registration transformation, and (iv) generate a signal to disable the surgical instrument when the mapped location of the distal end portion of the surgical instrument is substantially close to a boundary of the surgical site of the region of interest in the pre-operatively acquired 3D radiographic image.

In one embodiment, the system also includes an interlock device operatively associated with the surgical instrument and communicating with the controller. The interlock device in one embodiment includes an articulated/robotic arm that is programmed to control the surgical instrument to perform mastoidectomies based on pre-operative CT scans which have contoured to indicate desired surgical excavation, and disable the surgical instrument when the mapped location of the distal end portion of the surgical instrument is within a predetermined distance to the boundary of the surgical site in the region of interest in the pre-operatively acquired image volume. In one embodiment, the predetermined distance to the boundary of the surgical site is about 0.5 mm.

The system further includes an audio alarm coupled with the controller for generating an alarm when the mapped location of the surgical instrument is within a predetermined distance to the boundary of the surgical site in the acquired 3D radiographic image and a video frame coupled with the controller for displaying the precise anatomic location of the transgression as feedback to the operator.

Additionally, the system in one embodiment has two markers placed at surgically significant anatomic locations: the internal auditory canal and stylomastoid foramen of the ear portion of the patient, respectively. These two markers served as surgical targets for the purpose of estimating target registration error. Other anatomic landmarks which are stable and repeatably identifiable both on CT imaging scans and within the OR can also serve as surgical targets. They are any and/or all of the following: (i) the spine of Henle—a small outcrop of bone in the lateral external auditory canal, (ii) the lambda suture—a junction of three boney plates visible on the surface on the skull behind the ear, (iii) the capitulum of the stapes—the top portion of the third ear bone, (iv) the cochleaform process—a small outcropping of bone into which a tendon, the tensor tympani, attaches, (v) the pyramidal process—another small outcropping of bone into which a tendon, the stapedial, tendon attaches, (vi) the midpoint of the subiculum—a boney ridge which separates the oval window and the round window, and (vii) the neck of the malleus, a relatively constant position of the first ear bone.

The registration between the anatomic space and the CT image space is performed using various subsets of the fiducial markers. Each resulting transformation is applied to each surgical target marker in the anatomic space. The disparity between the transformed position and the measured position in the CT image space serves as a measure of registration error. Geometric arrangement of fiducial markers and their relation to target position affects error as expected from previous theoretical predictions [12]. Specifically, target registration errors are minimized with arrangement of the fiducial markers surrounding the surgical site of interest such that the centroid of the fiducial markers approximates the surgical site of interest. Also, registration accuracy is improved with the number of fiducial markers but with diminishing returns over a critical number. This becomes important in high-resolution CT scanning with the scannable volume is finite thus limiting the feasible number of markers. In one embodiment, with all 18 fiducial markers used for registration, that is each side of the ear portion of the patent has 9 fiducial markers, which are received in a first panel and a second panel of a fiducial frame, respectively, TRE for the surgically significant anatomic locations including an internal auditory canal and a stylomastoid foramen are TRE1=0.41 mm and TRE2=0.90 mm, respectively. In another embodiment, surrounding the side of interest, where a surgical site is located, of the ear portion of the patent with 9 markers and balancing this with a single, centrally placed marker on the contralateral side of the ear portion of the patient produces similar results with TRE1=0.52 mm and TRE2=0.90 mm. However, for an inverse situation, that is, surrounding the contralateral side of the surgical site of the ear portion of the patient with 9 fiducial markers and balancing the side of the surgical site of the ear portion of the patient with a single marker, it produces worse results with TRE1=1.26 mm and TRE2=1.80 mm for the internal auditory canal and stylomastoid foramen targets, respectively. These are the largest registration target errors occurred among 17 different configurations of 18 fiducial markers. TREs with a sub-millimeter accuracy (<1 mm) are reproducibly achievable using 5 fiducial markers surrounding the side of the surgical site of the ear portion of the patient and a single, centrally located fiducial marker balancing on the contralateral side of the ear potion of the patient for a critical number of 6 total fiducial markers. This makes image guided otologic surgery with submillimeter accuracy achievable with a minimally invasive fiducial frame.

The present invention, in another aspect, relates to a method for selectively disabling a surgical instrument operating in a surgical site of a region of interest of a patient thereof responsive to a position feedback of the surgical instrument that has a distal end portion. For example, the surgical instrument can be a surgical drill, a surgical scalpel and/or a suction device operable by a surgeon during surgery such as an otologic surgery to a human patient, and the region of interest of the patient corresponds to an ear portion of the patient. Prior to the otologic surgery, an Institutional Review Board (Vanderbilt University, Nashville, Tenn.) approval for surgical procedures of the otologic surgery for human patients is obtained and patient consent for the otologic surgery is acquired. A patient-specified LADS is constructed in a dental lab, for example, Peterman Dental Lab, after maxillary impressions are taken from the patient. The patient-specified LADS is then attached to a fiducial frame and mounted onto the maxilla of the patient, where the fiducial frame is configured such that when the number M of fiducial markers are received therein, the centroid of each fiducial marker approximates the surgical site of the ear portion of the patient and distance between two corresponding fiducial markers is maximized so as to minimize a target registration error. In one embodiment, each side of the ear portion of the patient is surrounded with nine fiducial markers. In addition, two surgical markers are placed in close proximity to 2 anatomically important structures, such as an internal auditory canal and a stylomastoid foramen of the ear portion of the patient.

Figure 4:
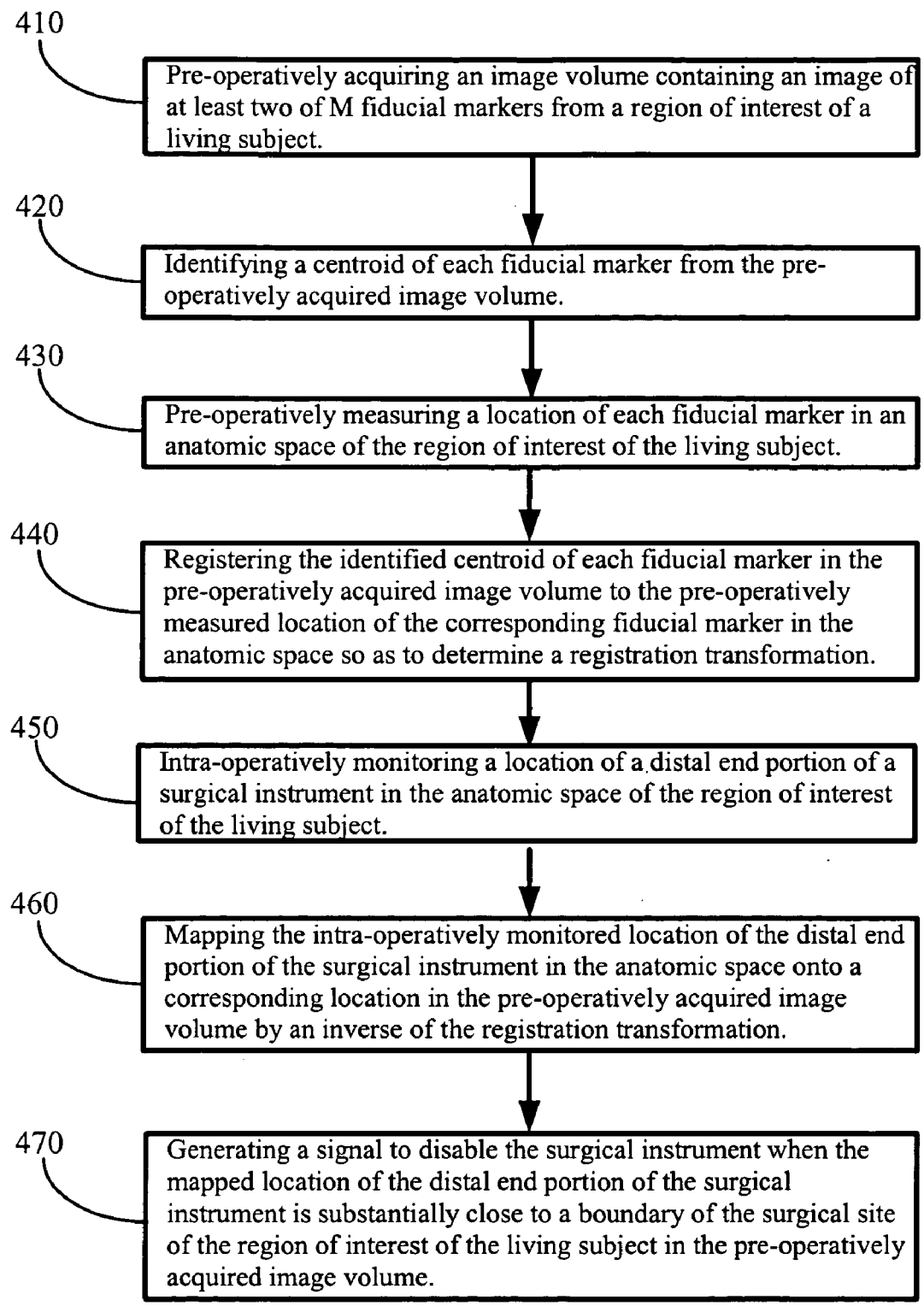
FIG. 4 shows a flowchart for selectively disabling a surgical instrument operating in a surgical site of a region of interest of a living subject according to one embodiment of the present invention.

In one embodiment, the method, as shown in FIG. 4, includes the following steps: at step 410, an image volume is acquired pre-operatively from the ear portion of the patient, where the pre-operatively acquired image volume contains the image of at least two of M fiducial markers. In one embodiment, three sequential CT imaging scans from the ear portion of the patient wearing the LADS and fiducial frame are taken. Other numbers of sequential CT imaging scans can also be taken. The fiducial frame is removed from and reattached to the LADS between two CT imaging scans. Multiple CT imaging scans are necessary in determining fiducial registration error (hereinafter "FRE") of the image space, which is employed to determine TRE. These FREs are averaged using sum of squares to determine an average FRE. At step 420, a centroid of each fiducial marker is identified from the pre-operatively acquired image volume. In one embodiment, the image volumes (3D CT images) are reconstructed from the CT imaging scans by utilizing a high-performance computer. On these reconstructed image volumes, voxels (i.e., a surgical site) that lie within the ear portion of the patient are selected by the surgeon. In other words, a surgical excavation, i.e., a mastoidectomy, is pre-operatively planned based on the radiographic images.

After pre-operatively acquiring image volumes of the patient, the LADS and the fiducial frame are removed and saved for the patient. In the OR, after performing a general anesthesia, the patient is re-fitted with his/her customized LADS and the fiducial frame. A location of each fiducial marker in an anatomic space of the ear portion of the patient is measured using an infrared optical tracking system, such as Polaris®, at step 430. The identified centroid of each fiducial marker in the pre-operatively acquired image volume is registered to the pre-operatively measured location of the corresponding fiducial marker in the anatomic space at step 440. The image registration determines a registration transformation and is performed by a computer in conjunction with the infrared optical tracking system and customized software. The registration transformation, in one embodiment, includes a rigid-body transformation. During the surgery, a location of the distal end portion of the surgical instrument in the anatomic space of the ear portion of the patient is monitored at step 450. In one embodiment, a high-speed surgical drill fitted with IR emitters is employed for the otologic surgery, and its tip location of the surgical drill is monitored by the infrared optical tracking system. At step 460, the intra-operatively monitored location of the distal end portion of the surgical instrument in the anatomic space is mapped onto a corresponding location in the pre-operatively acquired image volume by an inverse of the registration transformation. The mapping step in one embodiment is performed with the computer. When the mapped location of the surgical instrument is within a predetermined distance to the boundary of the surgical site in the pre-operatively acquired image volume, a controller, such as a computer coupled with the surgical instrument, generates a signal to disable the surgical instrument at step 470. In one embodiment, the predetermined distance is about 0.5 mm. For a typical surgical instrument, such as a surgical drill, with a length in the range of 15 to 20 cm, the predetermined distance of 0.5 mm is corresponding to a predetermined angle about (0.5 mm/200 mm)×360°=0.9°. Software codes and electric circuits for controlling the surgical instrument in the present invention are custom-designed. In the present invention, among other things, unique to the otologic surgery is that the surgical instrument, a high-speed surgical drill, can be quickly disabled to prevent collateral damage to healthy tissues. The disablement includes simply turning off the rotation of the bit using active braking when the surgical instrument leaves the surgeon-identified surgical site.

According to one embodiment of the current invention, anatomically significant landmarks, as described above, are intra-operatively and post-operatively acquired, respectively, in a blinded fashion, i.e., the surgeon points to a structure and an assistant acquires its position and label it. These data points are used to analyze the TRE of these anatomically significant points.

In addition, three endpoints of the surgery including (i) number of surgical transgressions beyond the safe surgical field, (ii) volume of tissues removed, and (iii) time of the surgery, are measured. Endpoint (i) is corresponding to an index of safety of the surgery and measured during the otologic surgery. Endpoint (ii) is assessed by obtaining post-surgical CT imaging scans to determine what percentage of the original planned excavation occurred. And endpoint (iii) corresponds to the operating time of the surgery from the start to the end of the surgery. Endpoints (i) and (iii) are corresponding to indices of efficiency of the surgery. Statistically appropriate comparisons are made after determining the distribution of the indices of efficiency of the surgery. Analysis of the endpoint data is performed with SigmaStat® Statistical Software (SPSS Science, Inc., Chicago, Ill.).

Figure 5:
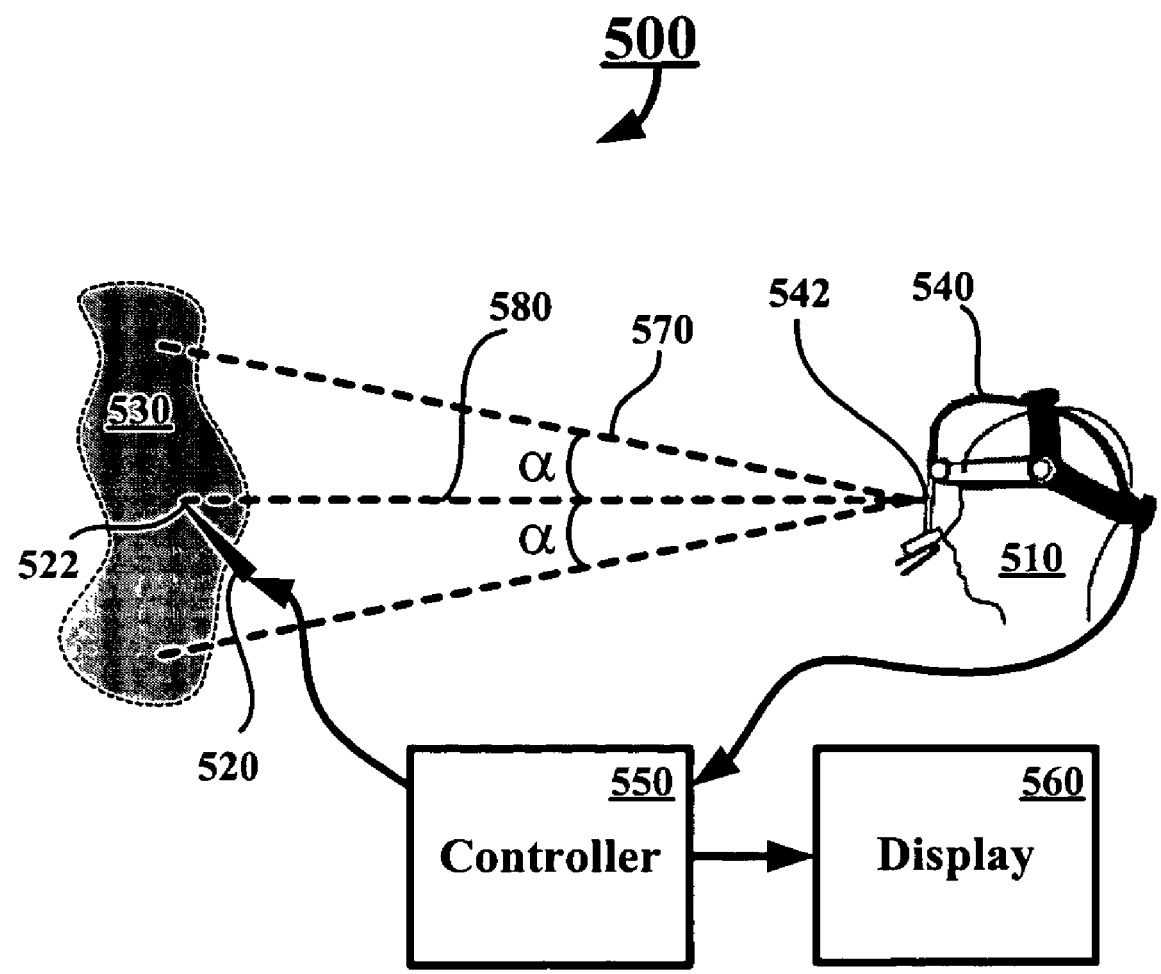
FIG. 5 shows schematically a system for selectively disabling a surgical instrument operating in a surgical site of a region of interest of a living subject according to one embodiment of the present invention.

Referring now to FIG. 5, a system 500 has a surgical instrument 520 operating in a surgical site 530 of a region of interest of a patient. The surgical instrument 520 has a distal end portion 522 and is operable by a surgeon 510 during a surgery. The surgical instrument 520 may be a commercially available surgical drill, a surgical scalpel, a suction device such as a surgical pump or tube, or other surgical instruments and any combination of them. The system 500 further has an eye-tracking device 540 for intra-operatively tracking the visual line of sight 570 of the surgeon 510 and a location of the distal end portion 522 of the surgical instrument 520 in the region of interest of the patient, respectively. In one embodiment, the eye-tracking device 540 includes a head-hold device, such as EyeLink® II, (SR Research, Ltd., Osgoode, Canada). Other eye-tracking devices can also be employed to practice the current invention. The system 500 also includes a controller 550 that is operatively coupled with the surgical instrument 520 and the eye-tracking device 540, respectively. The controller 550, such as a computer, is configured to perform during the surgery the step of processing the intra-operatively tracked visual line of sight 570 of the surgeon 510 and the location of the distal end portion 522 of the surgical instrument 520 in the region of interest of the patient to determine an angle, α, between a visual path 580 connecting a predetermined point 542 of the eye-tracking device 540 and the distal end portion 522 of the surgical instrument 520 in the region of interest of the patient and the line of sight 570 of the surgeon 510. The controller 550 is further configured to perform the step of generating a signal to disable the surgical instrument 520 when the angle α is larger than a predetermined angle as a threshold. In one embodiment, the controller 550 is associated with a computer.

In one embodiment, the system 500 has a display 560 communicatable with the controller 550 and the eye-tracking device 540 for displaying the tracked line of sight 570 of the surgeon 510 and the tracked location of the distal end portion 522 of the surgical instrument 520 in the region of interest of the patient, respectively.

The present invention, in one aspect, relates to a system for selectively disabling a surgical instrument operating in a surgical site of a region of interest of a patient, where the surgical instrument has a distal end portion and is operable by a surgeon during a surgery. In one embodiment, the system has a probe adapted for intra-operatively monitoring an electrophysiological condition of the patient in the region of interest, and a controller that is operatively coupled with the surgical instrument and the probe, respectively. The controller is further configured to perform during the surgery the steps of processing the intra-operatively monitored electrophysiological condition of the patient in the region of interest to identify a variation of the electrophysiological condition from an initial state of the patient in the region of interest, and generating a signal to disable the surgical instrument when the variation of the electrophysiological condition of the patient in the region of interest is greater than a predetermined value. The controller is associated with a computer.

In one embodiment, the probe has at least one needle electrode placed in the region of interest of the patent adapted for intra-operatively recording an electromyogram of electrical activities of muscles of the region of interest of the patient. When a myogenic potential is recorded by the at least one needle electrode, the controller will generate a signal to disable the surgical instrument.

The probe in another embodiment has a Doppler vascular probe adapted for intra-operatively monitoring a flow rate of blood vessels of the region of interest of the patient. When a variation of the flow rate of blood vessels of the region of interest of the patient is greater than a predetermined value, the controller will generate a signal to disable the surgical instrument.

In yet another embodiment, the probe has a temperature-sensing device adapted for intra-operatively measuring a temperature of tissues of the region of interest of the patient. When a variation of the tissue temperature of the region of interest of the patient is greater than a predetermined value, the controller will generate a signal to disable the surgical instrument.

In an alternative embodiment, the probe has an oxygenation detector adapted for intra-operatively detecting a venous oxygenation saturation and an arterial oxygenation saturation of the region of interest of the patient intra-operatively monitored by the oxygenation detector. When an alteration of the venous oxygenation saturation versus the arterial oxygenation saturation of the region of interest of the patient is identified, the controller will generate a signal to disable the surgical instrument.

The probe, in one embodiment, has a tissue boundary detector, where the tissue boundary detector includes at least one of an ultrasound sensing device, an infrared radiation sensing device, an ultraviolet radiation sensing device, a fluorescent radiation sensing device, and a video frame device. The tissue boundary detector is adapted for intra-operatively identifying a tissue type of tissues at the distal end portion of the surgical instrument in the region of interest of the patient. When the tissue type of tissues at the distal end portion of the surgical instrument is changed, the controller will generate a signal to disable the surgical instrument.

The present invention, among other things, discloses a system and method for selectively disabling a surgical instrument operating in a surgical site of a region of interest of a living subject, in response to a position feedback of the surgical instrument, an electrophysiological condition of the living subject in a region of interest, and a visual condition of sight of a surgeon who operates a surgery, respectively.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

REFERENCE LIST

[1]. Gering D T, Nabavi A, Kikinis R, Hata N, O'Donnell L J, Grimson W E, Jolesz F A, Black P M, Wells W M 3$^{rd}$, *An integrated visualization system for surgical planning and guidance using image fusion and an open M R, J Magn Reson Imaging* 2001 June; 13(6):967-75.
[2]. Lunsford L D, Kondziolka D, Bissonette D J, *Intraoperative imaging of the brain, Stereotact Funct Neurosurg* 66(1-3):58-64, 1996.
[3]. Spiegel E A, Wycis H T, and Marks M, Lee A. *Stereotactic apparatus for operations on the human brain, Science* 106:349-50, 1947.
[4]. Galloway R L, Maciunas R J and Edwards C A. *Interactive, Image-Guided Neurosurgery, IEEE Transactions on BME* 39(12):1126-1231, 1992.
[5]. Fried M P, Kleefield J, Gopal H, Reardon E, Ho B T, and Kuhn F A. Image-guided endoscopic surgery: results of accuracy and performance in a multi-center clinical study using an electromagnetic tracking system. *Laryngoscope* 107:594-601, 1997.
[6]. Maurer C R Jr, Fitzpatrick J M, Wang M Y, Galloway R L Jr, Maciunas R J and Allen, G S, *Registration of head volume images using implantable fiducial markers, IEEE Trans Med Imaging* 16(4):447-62, 1997.
[7]. West J B, Fitzpatrick J M, Toms S, Maurer, Jr, and Maciunas R J. *Fiducial point placement and the accuracy of point-based, rigid-body registration. Neurosurgery* 48:810-817, 2001.
[8]. West J, Fitzpatrick J M, Wang M Y, Dawant B M, Maurer C R Jr, Kessler R M, Maciunas R J, Barillot C, Lemoine D, Collignon A, Maes F, Suetens P, Vandermeulen D, van den Elsen P A, Napel S, Sumanaweera T S, Harkness B, Hemler P F, Hill D L, Hawkes D J, Studholme C, Maintz J B, Viergever M A, Malandain G, Woods R P, et al. *Comparison and evaluation of retrospective intermodality brain image registration techniques. J of Computer Assisted Tomography* 21(4):554-66, 1997.
[9]. Cawiano R R and Numa W A. *Efficacy of computed radiographic image-guided endoscopic sinus surgery in residency training programs. Laryngoscope* 110:1277-82, 2000.
[10]. Weinberg J S. Lang F F. Sawaya R. *Surgical management of brain metastases. Curr Oncol Rep* 3(6):476-83, 2001.
[11]. Wisoff J H, Boyett J M, Berger M S, Brant C, Li H, Yates A J, McGuire-Cullen P, Turski P A, Sutton L N, Allen J C, Packer R J, and Finlay J L. *Current neurosurgical management and the impact of the extent of resection in the treatment of malignant gliomas of childhood: a report of the Children's Cancer Group trial no. CCG-945. J of Neurosurg* 89(1):52-9, 1998.
[12]. West J B, Fitzpatrick J M, Toms S, Maurer, Jr, and Maciunas R J. *Fiducial point placement and the accuracy of point-based, rigid-body registration. Neurosurgery* 48:810-817, 2001.

What is claimed is:

1. A system for selectively disabling a surgical instrument operating in a surgical site of a region of interest of a living subject, wherein the surgical instrument has a distal end portion and is operable by a surgeon during a surgery, comprising:
    (a) an eye-tracking device operatively coupled with the surgical instrument for intra-operatively tracking the visual line of sight of the surgeon and a location of the distal end portion of the surgical instrument in the region of interest of the living subject, respectively; and
    (b) a controller operatively coupled with the surgical instrument and the eye-tracking device, respectively, and configured to perform during the surgery the steps of:
        (i) determining an angle between a visual path connecting a predetermined point of the eye-tracking device and the distal end portion of the surgical instrument in the region of interest of the living subject and the line of sight of the surgeon; and
        (ii) generating a signal to disable the surgical instrument when the angle is within a predetermined angle, but not outside of a boundary of the surgical site of the region of interest.

2. The system of claim 1, further comprising a display communicating with the controller and the eye-tracking device for displaying the tracked line of sight of the surgeon and the tracked location of the distal end portion of the surgical instrument in the region of interest of the living subject, respectively.

3. The system of claim 1, wherein the eye-tracking device comprises a sensor.

4. The system of claim 1, wherein the eye-tracking device comprises a head-hold device.

5. A method for selectively disabling a surgical instrument operating in a surgical site of a region of interest of a living subject, wherein the surgical instrument has a distal end portion and is operable by a surgeon during a surgery, comprising the steps of:
    (a) intra-operatively tracking the visual line of sight of the surgeon with an intra-operatively tracking means and a location of the distal end portion of the surgical instrument in the region of interest of the living subject, respectively;
    (b) determining an angle between a visual path connecting a predetermined point of the intra-operatively tracking means and the distal end portion of the surgical instrument in the region of interest of the living subject and the line of sight of the surgeon; and
    (c) generating a signal to disable the surgical instrument when the angle is within a predetermined angle, but not outside of a boundary of the surgical site of the region of interest.

* * * * *

UNITED STATES PATENT AND TRADEMARK OFFICE
CERTIFICATE OF CORRECTION

| | | |
|---|---|---|
| PATENT NO. | : 7,899,512 B2 | Page 1 of 1 |
| APPLICATION NO. | : 11/079898 | |
| DATED | : March 1, 2011 | |
| INVENTOR(S) | : Robert F. Labadie and J. Michael Fitzpatrick | |

It is certified that error appears in the above-identified patent and that said Letters Patent is hereby corrected as shown below:

In Column 1, Lines 35 to 38, delete:

"This present invention was made with Government support under Grant No. R21 EB02886-02 awarded by the National Institute of Health. The United States government may have certain rights to this invention pursuant to this grant."

In Column 1, Lines 35 to 38, insert:

--This invention was made with government support under Grant No. R21 EB02886-02 awarded by the National Institute of Health. The government has certain rights in the invention.--

Signed and Sealed this
Second Day of August, 2011

David J. Kappos
*Director of the United States Patent and Trademark Office*